United States Patent [19]  
Ward, III et al.

[11] Patent Number: 4,487,950  
[45] Date of Patent: Dec. 11, 1984

[54] METHOD FOR MAKING METHYLCHLOROSILANES

[75] Inventors: William J. Ward, III, Schenectady; George L. Gaines, Jr., Scotia; Alan Ritzer, Sand Lake, all of N.Y.

[73] Assignee: General Electric Company, Schenectady, N.Y.

[21] Appl. No.: 456,470

[22] Filed: Jan. 7, 1983

Related U.S. Application Data

[63] Continuation of Ser. No. 368,799, Apr. 16, 1982, abandoned.

[51] Int. Cl.$^3$ .............................. C07F 7/16  
[52] U.S. Cl. .................................... 556/472  
[58] Field of Search ....................... 556/472

[56] References Cited

U.S. PATENT DOCUMENTS

| | | | |
|---|---|---|---|
| 2,380,995 | 8/1945 | Rochow | 556/472 |
| 2,383,818 | 11/1943 | Rochow et al. | 556/472 UX |
| 2,389,931 | 11/1945 | Reed et al. | 556/472 UX |
| 2,443,902 | 6/1948 | Ferguson et al. | 556/472 UX |
| 2,464,033 | 3/1949 | Gilliam | 556/472 |
| 2,475,965 | 7/1949 | Hull et al. | 556/472 UX |
| 2,666,775 | 1/1954 | Nitzsche | 556/472 UX |
| 2,666,776 | 1/1954 | Nitzsche | 556/472 UX |
| 2,902,504 | 9/1959 | Nitzsche et al. | 556/472 UX |
| 3,133,109 | 5/1964 | Dotson | 556/472 UX |
| 3,141,899 | 7/1964 | Emblom et al. | 556/472 |
| 3,929,881 | 12/1975 | Kurata et al. | 556/472 UX |
| 4,088,669 | 5/1978 | Malek et al. | 556/472 UX |
| 4,218,387 | 8/1980 | Maas et al. | 556/472 |
| 4,314,908 | 2/1982 | Downing et al. | |

FOREIGN PATENT DOCUMENTS

| | | | |
|---|---|---|---|
| 28009 | 8/1982 | European Pat. Off. | 556/472 UX |
| 824049 | 4/1949 | Fed. Rep. of Germany | 556/472 UX |
| 410024 | 1/1974 | U.S.S.R. | 556/472 UX |

OTHER PUBLICATIONS

New Possibilities for the Preparation of a Contact Mass for the Direct Synthesis of Methylchlorosilanes, by Radosavljevic et al., Chemistry and Practical Uses of Organosilicon Compounds, Leningrad (1958), No. 6, pp. 37–43 (published 1961).

The Thermal Decomposition of Certain Metal Formates, Zapletal et al., Collection Czechoslov. Chem. Commun., vol. 22 (1957), pp. 171–174.

The Direct Synthesis of Organosilicon Compounds, by Zuckerman, pp. 383–432.

Synthesis of Organosilicon Monomers, Petrov et al., Authorized Translation from the Russian by C. Turton and T. I. Turton, Consultants Bureau, NY, (1964), pp. 26–61.

Organohalosilanes Precursors to Silicones, Voorhoeve, Chapter 4, pp. 121–151.

Synthesis and Reactions of the Silicon–Carbon Bond, Eaborn et al., Organometallic Compounds of the Group IV Elements, vol. I, Part I, AG MacDiarmid, ed. Dekker (1968), pp. 188–205.

A Study of the Direct Synthesis of Methylchlorosilanes, Rostsishevskii, Chemistry and Practical Use of Organosilicon Compounds, Leningrad, 1958, No. 1, Russian Article and Translation.

Primary Examiner—Paul F. Shaver  
Attorney, Agent, or Firm—William A. Teoli; James C. Davis, Jr.; James Magee, Jr.

[57] ABSTRACT

A process is provided for making methylchlorosilanes based on the reaction of methylchloride and particulated silicon, which has been contacted with a mixture of partially oxidized copper catalyst and copper formate. A reduction is achieved in the percent by weight of residue which are the silicon products in the methylchlorosilane crude having boiling points exceeding 70° C. at atmospheric pressure, while the weight percent of disilane in such residue cleavable to useful chlorosilane monomer is not adversely affected.

10 Claims, No Drawings

METHOD FOR MAKING METHYLCHLOROSILANES

CROSS REFERENCE TO RELATED APPLICATIONS

This application is a continuation, of application Ser. No. 368,799, filed Apr. 16, 1982, now abandoned.

Reference is made to copending application of Alan Ritzer and Heine Lapidot, Ser. No. 288,175, filed July 29, 1981, for A Catalyst for a Process for Producing Silicones, assigned to the same assignee as the present invention.

BACKGROUND OF THE INVENTION

The present invention relates to a method for making methylchlorosilanes based on the reaction of particulated silicon and methyl chloride in the presence of a copper-silicon catalyst. More particularly, the present invention relates to the use of particulated silicon which has been contacted with a mixture of partially oxidized copper catalyst and copper formate in the production of methylchlorosilanes.

Prior to the present invention, as shown by Rochow, Chemistry of the Silicones, Second Edition, (1951), John Wiley & Sons, New York Pages 36–46, methylchlorosilanes were made by the direct reaction of particulated silicon and methyl chloride in the presence of metallic copper or silver as a catalyst, while copper chloride or alloys of the aforementioned metal catalysts are often employed. In addition to dimethyldichlorosilane, a variety of other silanes can be formed such as tetramethylsilane, trimethylchlorosilane, methyltrichlorosilane, silicon tetrachloride, trichlorosilane, methyldichlorosilane and dimethylchlorosilane.

In addition to dimethyldichlorosilane, which is the preferred methylchlorosilane of the present invention, "residue" is produced during the formation of the methylchlorosilane crude. Residue means products in the methylchlorosilane crude having a bp >70° C. at atmospheric pressure. Residue consists of such materials as disilanes, for example, symmetrical 1,1,2,2-tetrachlorodimethyldisilane, 1,1,2-trichlorotrimethyldisilane, disiloxanes, disilmethylenes and other higher boiling species, for example, trisilanes, trisiloxanes, trisilmethylene, etc.

Experience has shown that certain components in the residue, as defined above, specifically 1,1,2,2-tetrachloro-dimethyldisilane, and 1,1,2-trichlorotrimethyldisilane can be "cleaved" in accordance with Bluestein, U.S. Pat. No. 2,709,176, French Pat. No. 1,447,304, or Japanese Pat. No. 1,783,419, to produce useful methylchlorosilane monomers. "Cleavability" means the weight percent of the aforementioned disilanes in the residue. Cleavage of the aforementioned disilanes can be effected by using the residue in a continuous stirred tank reactor employing a tertiary organic amine, for example tributylamine with a continuous feed of anhydrous hydrogen chloride.

In addition to making methylchlorosilanes based on the direct reaction between particulated silicon and methyl chloride in the presence of a copper catalyst to produce crude methylchlorosilanes having a reduced weight percent residue based on the total weight of the crude methychlorosilane and cleavability of such residue as previously defined, those skilled in the art also are interested in the T/D ratio of the methylchlorosilane crude. The T/D ratio is the ratio of methyltrichlorosilane to dimethyldichlorosilane in the crude methylchlorosilane reaction product. Accordingly, an increase in the T/D ratio indicates that there is a decrease in the production of the preferred dimethyldichlorosilane.

As shown in copending application Ser. No 288,175, improved results can be obtained in the reaction between particulated silicon and methylchloride by using partially oxidized copper as the copper catalyst. As taught in Ser. No. 288,175, the use of a partially oxidized, or cemented copper catalyst of specific particle-size distribution and exhibiting a minimum surface area (as measured by the BET method) provides an improvement in selectivity with respect to the T/D ratio, based on the reaction between particulated silicon and methylchloride.

The partially oxidized copper catalyst of Ser. No. 288,175 can be made by taking a solution of a copper compound and passing it over scrap iron which results in the deposition of metallic copper in the form of a fine precipitate. The precipitate is then subjected to a pyrometallurgical process which results in the partial oxidation of the cemented copper. There can be in the partially oxidized copper catalyst, a total of 77–87% by weight of copper, which can be in the combined or uncombined form, and preferably 83% by weight. The total reducing power of the partially oxidized copper catalyst is preferably 75–80, while a range of 70–90 can be used. The total reducing power "TRP", the percent cuprous oxide, can be determined by titration with a standard iron sulfate solution using Ferroin indicator.

The metallic copper content of the partially oxidized copper catalyst can vary from 10–20% by weight, and preferably 15–20% by weight of the partially oxidized copper catalyst. The partially oxidized copper catalyst can contain 30–50% by weight of cuprous oxide, while 39–50% by weight of cuprous oxide is preferred. The partially oxidized copper catalyst also can contain 30–50% by weight of cupric oxide, while 35–43% by weight of cupric oxide is preferred.

The partially oxidized copper catalyst utilized in the practice of the present invention can be further characterized as comprising partially oxidized copper particles having a surface area of at least 3.5 $m^2$/gram as determined by the Brunauer, Emmett and Teller, Nitrogen Adsorption Method, Jour. Am. Chem. Soc., Vol. 60, p. 309, (1938). In addition, the partially oxidized copper catalyst has a particle size distribution of particles which are less than 35 microns in diameter and greater than 0.7 microns in diameter. Further, 50% of the particles are in the range of from 4–7 microns and the area mean diameter of the particles varies from 3.0–5.5 microns.

Generally, the chloride content of the partially oxidized copper catalyst should be in the range of from about 0–0.2%, and preferably from 0–0.1% by weight and the sulfate content varied from 0–1.5% by weight and preferrably from 0–0.8% by weight. The iron content of the copper catalyst can vary from 0 to 1.5% by weight and preferably from 0–1% by weight. The partially oxidized copper catalyst can have up to about 0.2% by weight of lead and up to about 0.5% by weight of tin, while the water content can vary from 0–0.75% by weight. Other desirable measurements of the partially oxidized copper catalyst are that the apparent density should be from 1.2–1.4 grams per cc and the Fisher number as determined by Fisher Scientific Company Sub Seive Sizer, should vary from 1.8–2.4 micrometers (μm) which is a determination of the air permeability of the powder.

As taught in copending application Ser. No. 288,175, methylchlorosilanes made by the direct method of Rochow utilizing the above-mentioned partially oxidized copper catalyst provide methylchlorosilane mixtures having satisfactory T/D ratio. However, we have found that the weight percent residue of the methylchlorosilane mixtures utilizing the partially oxidized copper catalyst often exceeds acceptable limits.

Additional studies have been conducted to improve the performance of copper as a catalyst for the direct reaction between particulated silicon and organic chloride as shown in Chemistry and Practical Uses of Organosilicon Compounds, V. 1, Leningrad (1958) by P.S. Rostsishevskii, A Study of the Direct Synthesis of Methylchlorosilanes, Institute of Artificial Resins, Warsaw, pages 42–59. Contact masses were used by Rostsishevskii with methyl chloride, which were obtained by heating mixtures of particulated silicon with copper formate.

We have found that the employment of copper formate in place of the partially oxidized copper catalyst in the direct method of Rochow, results in a significant reduction in the weight percent residue produced in the crude methylchlorosilane mixture. However, we have further found that the cleavability of such residue is significantly reduced as compared to the cleavability of the residue provided by the partially oxidized copper catalyst.

The present invention is based on the discovery that a mixture of the partially oxidized copper catalyst and copper formate can provide methylchlorosilane crude having a significant reduction in the weight percent residue, as compared to the use of the partially oxidized catalyst alone. In addition, the cleavability of the residue produced by the use of the mixture of partially oxidized copper catalyst and copper formate is substantially the same as the cleavability of the residue made by using the partially oxidized copper catalyst. Accordingly, a substantial increase in the production of dimethyldichlorosilane and usable methylchlorosilane monomer is provided by the practice of the present invention by a combination of partially oxidized copper catalyst and copper formate. Further improvements such as the batch weight percent of silicon utilization, maximum rate, as well as a substantial enhancement in most situations in the T/D ratio also have been found.

STATEMENT OF THE INVENTION

In the method for making methylchlorosilane crude having at least 70% by weight of dimethyldichlorosilane, by reacting methylchloride with particulated silicon in the presence of an effective amount of a copper-silicon catalyst, based on the use of a partially oxidized copper catalyst, whereby a significant amount of cleavable disilane containing residue is formed in the methylchlorosilane crude having a boiling point of >70° C. under atmospheric conditions, resulting in an overall reduction in the weight percent of recoverable dichlorosilane from the methylchlorosilane crude, the improvement which comprises, utilizing copper formate in combination with the partially oxidized copper catalyst, whereby methylchlorosilane crude is produced having a significant reduction in the weight percent of such residue, based on the total weight of methylchlorosilane crude, while the weight percent of cleavable disilane in such residue is substantially the same as that provided by the partially oxidized copper catalyst.

Although methylchloride is preferably used in the practice of the present invention, other $C_{(1-4)}$ alkylchlorides, for example, ethylchloride, propylchloride, etc., also can be used.

Methylchloride, or an inert gas, such as argon, can be initially used to fluidize the bed of silicon particles and the catalyst particles in the column. The fluidized bed is substantially made up of silicon and catalyst particles. The silicon particles are composed of silicon which is present in the form of particles having a size below 700 microns, with an average size of greater than 20 microns and less than 300 microns in size. The mean diameter of the silicon particles is preferably in the range of 100 to 150 microns.

Silicon is usually obtained at a purity of at least 98% by weight of silicon and it is then comminuted to particles of silicon in the above-described range, and is fed into an appropriate reactor as needed. Although a fluidized bed is preferred, the process of the present invention can be utilized in other types of reactors, such as a fixed bed and a stirred bed. A fluidized reactor is preferably utilized since the maximum selectivity and the maximum amount of dimethyldichlorosilane is obtained. The process of the instant case is carried out at a temperature in the range of 250°–350° C. and more preferably at a temperature range of 280°–330° C. Reaction can occur under continuous conditions or as a batch reaction.

It is also advisable to carry out the process under pressure since this increases the yield and conversion of methylchloride to methylchlorosilanes. It is generally desired to have the process carried out under 1–10 atmospheres of pressure and more preferably at a pressure of 1–5 atmospheres of pressure gauge, that is pressure above atmospheric pressure. Under these conditions, there is fed into the reactor, the desired amount of particulated silicon as needed as well as the desired amount of "copper catalyst", which hereinafter means a mixture of 0.25 to 4 parts of copper formate, per part of partially oxidized copper, as previously defined. If desired, the partially oxidized copper catalyst and copper formate can be separately introduced into the reactor. There can be used from about 0.5 to 10 parts of copper catalyst, per 100 parts of silicon powder.

Methylchloride gas is continually passed through the reactor so as to fluidize the reaction mass and there is passed out of the reactor, gaseous methylchlorosilanes as well as the unreacted methylchloride. The gaseous mixture of reaction particulate is passed out of the fluidized reactor and is passed through one or more cyclones so as to separate the larger particles of materials from the product gas stream. These particles can be returned to the reactor for further utilization in the process so as to maximize the yield of dimethyldichlorosilane from the silicon. Smaller particles are passed out with the product stream and the stream is subsequently condensed.

Purified methylchloride is heated and recycled through the fluidized reactor for the further production of methylchlorosilane. The crude methylchlorosilanes stream is passed to a distillation column so as to distill out in essentially pure form various chlorosilane fractions produced by the process. It is necessary to distill and purify the the dimethyldichlorosilanes and the other chlorosilanes so that they can be utilized in the process for producing silicone materials as has been discussed previously.

The copper formate utilized in the practice of the present invention can be further characterized as a substantially anhydrous granular material derived from technical grade cupric formate dihydrate (Cu(CHO$_2$)$_2$.2H$_2$O) or cupric formate tetrahydrate (Cu(CHO$_2$)$_2$.4H$_2$O) and exhibiting a BET surface area of from 0.5–20 m$^2$/gram by the nitrogen adsorption method.

The copper catalyst can be in the form of a dry blended mixture of partially oxidized copper catalyst and copper formate, or the partially oxidized copper catalyst and copper formate can be blended together in the presence of an inert organic solvent, such as hexane, to improve blending. Preferably, 1.5 to 2.5 parts of copper formate per part of partially oxidized copper can be used to make the copper catalyst.

In addition to the copper catalyst, there also can be used 0.005 to 2 parts of powdered zinc metal promoter, per 100 parts of powdered silicon.

It should also be noted that in the above-described process by which methylchlorosilanes are produced, the above-described range of copper catalyst per 100 parts of powdered silicon can vary widely.

Those skilled in the art know that the dimethyldichlorosilane made in accordance with the practice of the present invention can be hydrolyzed in accordance with the teaching of Rochow as previously shown to provide a wide variety of useful products such as silanol-terminated polydimethylsiloxne fluids, gums and greases.

In order that those skilled in the art will be better able to practice the invention, the following examples are given by way of illustration and not by way of limitation. All parts are by weight.

EXAMPLE 1

Experimental 1½ inch ID fluid bed reactors and a 1 inch ID stirred bed reactor were set up to determine the effectiveness of copper formate and a mixture of copper formate and partially oxidized copper catalyst for the production of methylchlorosilane crude obtained from the reaction of silicon powder and methyl chloride.

The copper formate was obtained from the ARS Chemical Company of Providence, R.I. and was dehydrated by heating cupric formate tetrahydrate at 90° C. for 24 hours. The partially oxidized copper catalyst was obtained from the Glidden Company, Cleveland, Ohio and was typically a material which analyzed as follows, where "TRP", or total reducing power, "BET", or Brunauer, Emmet and Teller and "Fisher Number" are as previously defined:

| TRP | Total Cu | Cu$^o$ | Cu$_2$O | CuO | App. Density (gm/cm$^3$) | BET Surface Area m$^2$/g | Part Size ($\mu$m) Median | Fisher Number |
|---|---|---|---|---|---|---|---|---|
| 73.20 | 83.4 | 14.47 | 40.64 | 41.40 | 1.27 | 5.2 | 4.6 | 2.20 |
| — | 82.06 | 12.33 | 33.96 | 49.54 | 1.36 | 4.1 | 6.0 | 3.35 |
| 77.90 | 84.0 | 16.78 | 40.14 | 39.48 | 1.24 | 4.5 | 4.6 | 2.15 |
| 76.63 | 83.5 | 16.68 | 39.07 | 40.18 | 1.43 | 3.7 | 6.6 | — |
| 73.50 | 83.55 | 15.10 | 39.52 | 41.75 | 1.23 | 3.8 | 4.5 | 2.00 |

The silicon powder utilized in the catalyst evaluation had an average surface area of 0.5 m$^2$/g and a maximum particle size of up to 70 microns. Catalyst effectiveness was determined by measuring the maximum normalized rate of crude methylchlorosilane production (grams of crude/grams of silicon in reactor/hour), "percent silicon utilization", T/D, "residue", and "cleava- bility".

The fluid bed reactor consisted of 3 concentric 20 inch glass tubes having ID's of 2¾ inch, 2 inch and 1½ inch. The 1½ inch ID reactor tube had a distribution plate at the middle of the tube which was within the 2 inch ID tin oxide coated furnace tube which was enclosed within the 2¾ inch ID insulating tube.

A mixture of 20 grams of silicon powder as defined above, 0.1 gram zinc powder, 0.62 gram partially oxidized copper catalyst, having a total of about 84% by weight of combined and uncombined copper and 1.21 grams of anhydrous cupric formate were dry blended together by stirring with a spatula and by vigorous shaking in a closed jar. The blended mixture was poured into the fluidized bed reactor which was at 300° C. and through which argon gas was flowing. Similar dry blended mixtures were prepared for the stirred bed reactor. Copper formate decomposition was complete in about 5 minutes as shown by the deposit of metallic copper on the inside walls of the readily viewed interior of the fluidized-bed reactor.

Methylchloride was then introduced into the fluid bed reactor at a rate of 1.5 cc per second and the argon flow discontinued. After a period of 89 minutes, the first drop of crude methylchlorosilane was recovered by condensation at −20° C. The reaction was allowed to continue for 28 hours. There was obtained 59.8 grams of crude chlorosilanes consisting of dimethyldichloro silane, methyltrichlorosilane and the following monomers: Me$_4$Si, HSiCl$_3$, Me$_2$HSiCL, Me$_3$SiCL and SiCL$_4$. This corresponded to a silicon utilization of 68% by weight.

The maximum normalized rate of crude chlorosilane production during the fluid bed run was 0.255 grams of crude/grams of silicon in the reactor per hour which occurred at a silicon utilization of 61%. For purposes of comparing rates of crude production, a reaction rate constant was used which is defined by the empirical kinetic rate expression for the reaction between powdered silicon and organic chloride shown by R. Voorhoeve, Organohalosilanes: Precursors to Silicones, Elsevier, (1967). Applying the aforementioned empirical kinetic rate expression, a normalized rate constant of 39.5 grams crude/grams silicon/hour was obtained.

The crude chlorosilane mixtures were analyzed by gas chromatography utilizing Hewlett-Packard and Perkin Elmer gas chromatographs equipped with packed columns and thermal conductivity detectors. The fluid bed methylchlorosilane crude provided a T/D of 0.072, a residue of 3.05 weight percent. The aforementioned residue was found to have a potential cleavability of 86%, based on the presence of 86% by weight of symmetrical tetrachlorodimethyldisilane and trichlorotrimethyldisilane.

The stirred bed reactor consisted of a stainless steel tube approximately 18 inches long with a 1 inch ID. It was equipped with dual zone electrical heaters to provide a reaction zone of about 1"×6". It was also equipped with a helical stainless steel stirrer.

The stirred bed reactor was preheated to 300° C. under a purge of nitrogen until stabilized. The reactor was then charged with a preblended mixture of 50 grams powdered silicon, 0.25 gram zinc, 1.55 grams partially oxidized copper catalyst, and 3.02 grams of anhydrous cupric formate.

When the reaction zone temperature had stabilized at 300° C. for 15 to 30 minutes, methyl chloride was introduced into the stirred bed at a feed rate of 12.5 grams per hour. There was obtained 165 grams of methylchlorosilane crude utilizing a condenser maintained at −20° C.

In accordance with the procedure of copending application Ser. No. 288,175, there was charged to the fluid bed reactor, a mixture of 20 grams of silicon powder, 0.1 gram of powdered zinc, and 1.26 grams of partially oxidized copper catalyst. The first drop of crude methylchlorosilane appeared in 66 minutes. The maximum normalized rate constant was found to be 29 grams of crude methylchlorosilane/grams of silicon/hour and the silicon utilization was found to be 55%. The T/D was found to be 0.141, the residue was 5.9 weight percent and the cleavability was 85%.

Additional fluid bed and stirred bed reactor runs were made. The results of the fluid bed reactors (1, 3) and the stirred bed reactor (2) runs are shown in the following table, where "Maximum Rate" is a rate constant $K_p$, grams of crude/grams of Si per hour, "POCC" is partially oxidized copper catalyst, and "T/D", "Residue" and "Cleavability" are as previously defined:

TABLE I

| Weight | Reactor | Maximum Rate | Si Utilization at Max Rate | Overall T/D | Residue | Cleavability | Final Utilization |
|---|---|---|---|---|---|---|---|
| 100% POCC | 1 | 20 | 28 | 0.121 | 5.5 | 82 | 39 |
|  | 1 | 29 | 30 | 0.141 | 5.9 | 85 | 55 |
|  | 2 | 20 | 38 | 0.113 | 7.2 | 86 | 39 |
|  | 3 | 52 | 40 | 0.059 | 7.5 | 91 | 55 |
|  | 3 | 13 | 12 | — | — | — | 19 |
| 20% Copper Formate 80% POCC | 1 | 60 | 24 | 0.068 | 5.0 | — | 67 |
| 50% Copper Formate 50% POCC | 1 | 71 | 42 | 0.059 | 3.1 | 87 | 72 |
|  | 1 | 54 | 41 | 0.066 | 3 | 90 | 71 |
|  | 2 | 54 | 29 | 0.085 | 3 | 86 | 73 |
|  | 3 | 35 | 21 | 0.069 | 2.4 | 77 | 46 |
| 75% Copper Formate 25% POCC | 3 | 20 | 20.5 | .062 | 2.2 | 72 | 36.9 |
| 100% Copper Formate | 3 | 10 | 2 | 0.058 | 3.8 | 16 | 7 |
|  | 3 | 10 | 2 | — | 2.5 | 29 | 14 |

The above results show that the mixture of the partially oxidized copper catalyst and copper formate significantly improves the maximum rate of methylchlorosilane production, the silicon utilization at the maximum rate and final silicon utilization and T/D ratio. In addition, the combination of copper formate and the partially oxidized copper catalyst achieves the percent residue advantages of the copper formate, while retaining the cleavability advantages of the partially oxidized copper catalyst.

EXAMPLE 2

The following speculative example illustrates the practice of the present invention under continuous conditions in a fluid bed reactor:

There is fed per hour into a fluid bed reactor having a pressure of 30 pounds per square inch gauge, and at a temperature of 300° C., a feed mixture of 100 parts of powdered silicon, 2.4 parts of anhydrous copper formate, 1.2 parts of partially oxidized copper catalyst and 0.2 part of powdered zinc per hour. There is also introduced at the bottom of the reactor 600 parts of methyl chloride per hour. There is recovered at the top of the reactor 240 parts of unreacted methyl chloride per hour which is recycled and approximately 460 parts per hour of crude methylchlorosilanes.

The above reaction components are found to provide a 2% loading of total copper, based on the equivalent weight of copper obtained from the copper formate and partially oxidized copper catalyst used in the reaction, and a 0.2 percent by weight of zinc. The crude methylchlorosilane which is recovered is found to have a 3% by weight residue, which has a 90% by weight cleavability, based on the total weight of the residue, while the balance of the methylchlorosilane obtained from the crude mixture has a T/D ratio of 0.06.

Although the above examples are directed to only a few of the very many variables utilized in the practice of the present invention, it should be understood that the present invention is directed to the use of a broader variety of alkyl chlorides, partially oxidized copper catalysts, and proportions of such partially oxidized copper catalyst to copper formate.

What we claim as new and desire to secure by Letters Patent of the United States is:

1. A method for making methylchlorosilanes comprising, effecting reaction between methylchloride and powdered silicon in the presence of a copper-silicon catalyst, where the copper-silicon catalyst is based on the use of a particulated mixture of silicon, partially oxidized copper and copper formate.

2. A method in accordance with claim 1, where the methylchlorosilane is methylchlorosilane crude having at least 70% by weight of dimethyldichlorosilane.

3. A method in accordance with claim 1, where there is utilized in the copper-silicon catalyst mixture, 0.25 to 4 parts of copper formate, per part of partially oxidized copper.

4. In the method for making methylchlorosilane crude having at least 70% by weight of dimethyldichlorosilane, by reacting methylchloride with particulated silicon in the presence of an effective amount of a coppersilicon catalyst, based on the use of a partially oxidized copper catalyst, whereby a significant amount of cleavable disilane containing residue is formed in the methylchlorosilane crude having a boiling point of >70° C. under atmospheric conditions, resulting in an overall reduction in the weight percent of recoverable dichlorosilane from the methylchlorosilane crude, the improvement which comprises, utilizing copper formate in combination with the partially oxidized copper catalyst, whereby methylchlorosilane crude is produced having a significant reduction in the weight percent of such residue, based on the total weight of methylchlorosilane crude, while the weight percent of cleavable disilane in such residue is substantially the same as that provided by the partially oxidized copper catalyst.

5. A method in accordance with claim 1, where the catalyst mixture contains an effective amount of a zinc promoter.

6. The method of claim 1, where the partially oxidized copper catalyst has a surface area of at least 3.5 square meters per gram.

7. A method in accordance with claim 1, where there is used sufficient copper formate and partially oxidized copper catalyst to provide 0.5 to 10 parts of such copper catalyst, per 100 parts of particulated silicon.

8. A method in accordance with claim 1, which is performed in a continuous manner.

9. A method in accordance with claim 1, which is performed in a fluid bed reactor.

10. A method in accordance with claim 1, which is performed in a stirred bed reactor.

* * * * *

UNITED STATES PATENT AND TRADEMARK OFFICE
CERTIFICATE OF CORRECTION

PATENT NO. : 4,487,950

DATED : Dec. 11, 1984

INVENTOR(S) : William J. Ward, III et al.

It is certified that error appears in the above-identified patent and that said Letters Patent is hereby corrected as shown below:

Title Page:
Item No. [75] Inventors: "George L. Gaines, Jr., Scotia;" should be deleted.

Signed and Sealed this

Seventh Day of September, 1993

*Attest:*

BRUCE LEHMAN

*Attesting Officer*  *Commissioner of Patents and Trademarks*